(12) United States Patent
Morre'

(10) Patent No.: US 6,361,961 B1
(45) Date of Patent: Mar. 26, 2002

(54) GRAVITY RESPONSIVE NADH OXIDASE OF THE PLASMA MEMBRANE

(75) Inventor: D. James Morre', West Lafayette, IN (US)

(73) Assignee: The United States of America as represented by the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/560,532

(22) Filed: Apr. 25, 2000

(51) Int. Cl.$^7$ .................................................. C12Q 1/26
(52) U.S. Cl. ............................................. 435/25; 435/4
(58) Field of Search ............................... 435/4, 15, 18, 435/25, 14

(56) References Cited

PUBLICATIONS

Garcia, C. et al., Plant Physiol. Biochem. (1999) vol. 37, pp. 551–558.*

Chapes, S.K. et al., Trans. of the Kansas Acad. of Sci., (1993) vol. 96, pp. 74–79.*

Rijken, P.J. et al., Exp. Cell Res., (1993) vol. 204, pp. 373–377.* de Groot, R.P et al., Exp. Cell Res., (1991) vol. 197, pp. 87–90.*

Fukaki, H, et al., Plant Cell Physiol., (1997) vol. 38, pp. 804–810.*

* cited by examiner

Primary Examiner—Jon P. Weber
Assistant Examiner—Harry Guttman
(74) Attorney, Agent, or Firm—James J. McGroary

(57) ABSTRACT

A method and apparatus for sensing gravity using an NADH oxidase of the plasma membrane which has been found to respond to unit gravity and low centrifugal g forces. The oxidation rate of NADH supplied to the NADH oxidase is measured and translated to represent the relative gravitational force exerted on the protein. The NADH oxidase of the plasma membrane may be obtained from plant or animal sources or may be produced recombinantly.

5 Claims, 4 Drawing Sheets

US 6,361,961 B1

GRAVITY RESPONSIVE NADH OXIDASE OF THE PLASMA MEMBRANE

ORIGIN OF THE INVENTION

This invention was made with Government support under contract NAG8-1147 awarded by the National Aeronautics and Space Administration. The Government has certain rights under this invention.

BACKGROUND OF THE INVENTION

1. Field of the Invention

The present invention relates to a method of sensing gravity and more particularly, to a method of and apparatus for sensing gravity using an NADH oxidase of the plasma membrane.

2. Background of the Invention

Gravity determination and methods of measuring gravity are well known in the art. However, currently there are no biological gravity sensors available. Thus far, modern gravitational studies in plants have focused on molecular approaches with emphasis on genetic analyses in Arabadopsis (Fukaki H., Fujisawa H., and Tasaka M., The RHG gene is involved in root and hypocoytl gravi-tropism in *Arabadopsis thaliana*, 38 Plant Cell Physiol 804–810 (1997). While the identification of the Arabadopsis genes involved in gravi-perception and response will be helpful to understand root and shoot gravitropism, there is still no indication of what protein or proteins might be involved, and thus no previous disclosure or suggestion of a useful protein which would be helpful in biological gravitational sensing.

Gravity response is, of course, not limited to plants. A number of development and growth responses (axis formation and establishment of polarity in amphibia and birds, for example) are know to respond to gravitational stimuli. (McLaren A., *Development Biology and Microgravity*, In: L. G. Griarty. Biology in Microgravity, European Space Agency, Paris pp. 239–242, (1989). Behavior of cultured mammalian cells also has been shown to respond to micro-gravity with most of the responses involving cell proliferation and the production and/or response to mitogenic stimuli and growth factors. Gmunder F. K., Cognoli A., *Cultivation of Single Cells in Space*, 3 Appl. Microgravity Tech., 115–122, (1988). However, these previous findings have also not resulted in the development of any system which would be useful in developing an effective biological gravity sensor.

A biological gravity sensor encompassing a protein that responds to changes in gravity could have wide-spread application in space exploration and medical applications. In addition, a protein gravity sensor could be used in applications requiring a miniaturized sensor.

SUMMARY OF THE INVENTION

It is therefore an object of the invention to provide a method of biologically sensing gravity.

It is a further object of the invention to provide a simple and effective miniaturized gravity sensor.

A further object of the invention is to provide a method of sensing responses to micro-gravity in living organisms.

It has been found that the NADH oxidase protein, preferably from the plasma membrane, exhibits a response to unit gravity and low centrifugal g forces. Specific protein sources include but are not limited to intact soybean hypocotyl sections, isolated vesicles of plasma membranes from soybean hypocotyl sections and from HeLa cells (cultured human cervical carcinoma).

Accordingly, there is provided a method of sensing gravity utilizing the NADH oxidase protein. An apparatus incorporating this method is also disclosed. The method comprises delivering external NADH to the NADH oxidase, measuring the rate of NADH oxidation by the protein, and translating the rate of oxidation to represent the relative gravitational force exerted on the protein. An apparatus incorporating this method is also disclosed.

Further features and advantages of the present invention will be set forth in, or apparent from, the detailed description of preferred embodiments thereof which follows.

DESCRIPTION OF THE PREFERRED EMBODIMENTS

Figure 1:
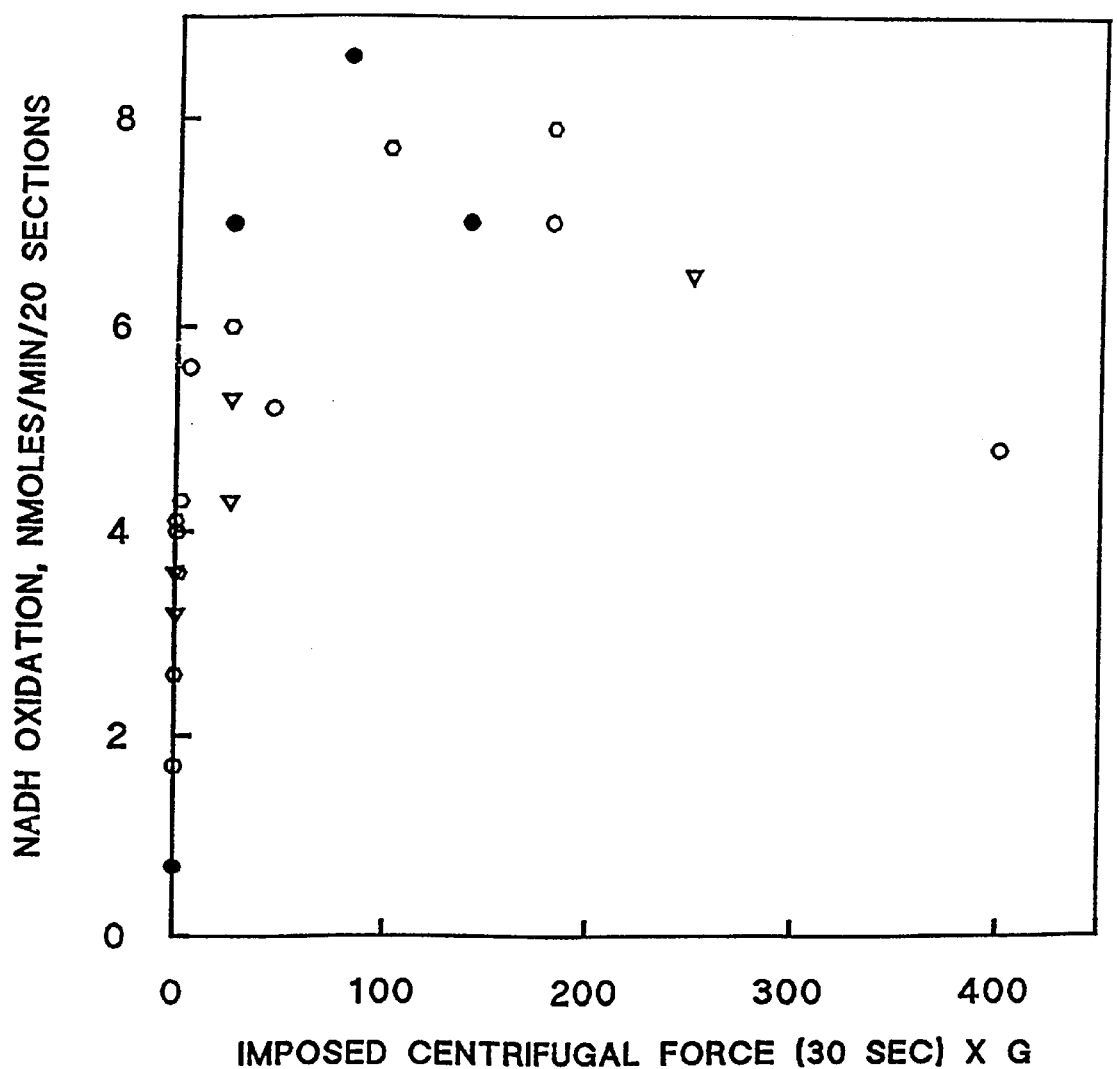
FIG. 1 is a graph showing the NADH oxidation rate in whole soybean hypocotyl segments as a function of centrifugal force.

According to the present invention, there is provided a method of sensing gravity comprising delivering external NADH to an NADH oxidase protein, measuring the rate of NADH oxidation by the protein, and translating the rate of oxidation to represent the relative gravitational force exerted on the protein. An apparatus incorporating this method is also disclosed.

The oscillating hydroquinone (NADH) oxidase protein is preferably present in the plasma membrane and plasma membrane precursors and derivatives of both plant and animal sources. In addition, the NADH oxidase may be prepared by recombinant techniques. NADH activity can be determined from the rate of NADH oxidation. Since NADH is an impermeant substrate, this activity can be determined using intact tissue sections. The activity may also be determined using isolated plasma membrane vesicles and purified and partially purified protein in solution.

In order to carry out the invention, a suitable source of NADH oxidase is necessary. In a preferred embodiment, the NADH oxidase was obtained from whole sections and isolated plasma membranes of soybean hypocotyl sections.

Soybean seeds grown in darkness for 4–5 days provide hypocotyl segments which can be used as whole sections or for isolating the plasma membranes. The isolated plasma membranes are preferably obtained by homogenizing hypocotyl segments in a medium containing buffer, sucrose, potassium chloride, and magnesium chloride, followed by filtration and centrifugation. Plasma membrane vesicles are advantageously obtained by aqueous two-phase partition of the microsomal pellet produced during centrifugation.

Measuring the rate of NADH oxidation is a convenient method of determining NADH oxidase activity. Externally supplied NADH is preferably used to initiate the oxidation reaction. In preferred embodiment, the activity of NADH is determined from changes in concentration using known spectrophotometric methods. However, NADH activity has been found to oscillate with a temperature compensated period of 24 minutes. To counter this periodic oscillation, activity assays are preferably carried out to overlap at least one full period of activity.

In order to translate the NADH oxidase activity to represent the relative gravitational force exerted on the sample, the effect of gravi-stimulation on activity must be known. The effect of unit gravity on whole hypocotyl sections is preferably determined by measuring the activity after changing the hypocotyl orientation. Activity was found to increase by about 50% when the hypocotyl sections were inverted and incubated for 30 minutes. After measuring activity for 30 minutes, the sections were again oriented right-side up and incubated for 30 minutes. The rate of NADH oxidation returned to the initial rates when the sections were returned to their initial right-side up orientation.

|  | | NADH oxidation, nmoles/min/20 sections ± std. dev. | | | | | |
| --- | --- | --- | --- | --- | --- | --- | --- |
| CYCLES | n | RSU | USD | Δ | RSU | USD | Δ |
| One cycle | 10 | 9.2 ± 1.8 | 13.2 ± 2.4 | 4.0 ± 1.2 | | | |
| Two cycles | 5 | 8.2 ± 0.003 | 12.6 ± 4.0 | 4.0 ± 2.2 | 9.0 ± 1.4 | 12.2 ± 3.0 | 3.2 ± 1.2 |

Figure 2:
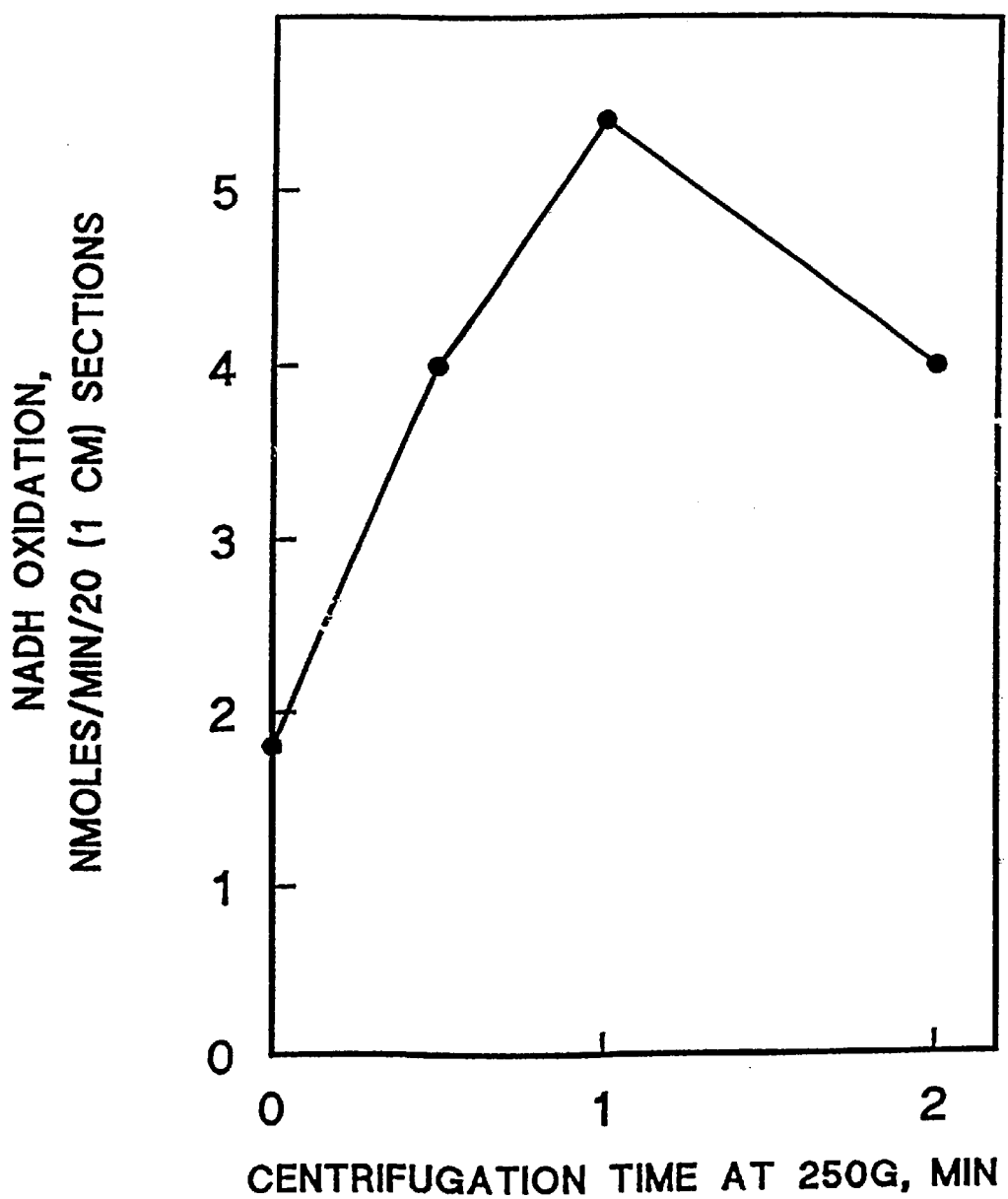
FIG. 2 is a graph showing the NADH oxidation rate in whole soybean hypocotyl segments as a function of centrifugal time.

The effect of centrifugation on whole sections and isolated plasma membrane vesicles is also preferably obtained by measuring the change in activity after centrifugation. Whole hypocotyl sections centrifuged for brief periods of time at low g forces were found to exhibit increased NADH oxidase activity. The activity was found to be dependent on both the force (FIG. 1) and time (FIG. 2) of centrifugation. Optimum stimulation was observed when sections were subjected to between 50 and 250 g for approximately 30 seconds.

Figure 3:
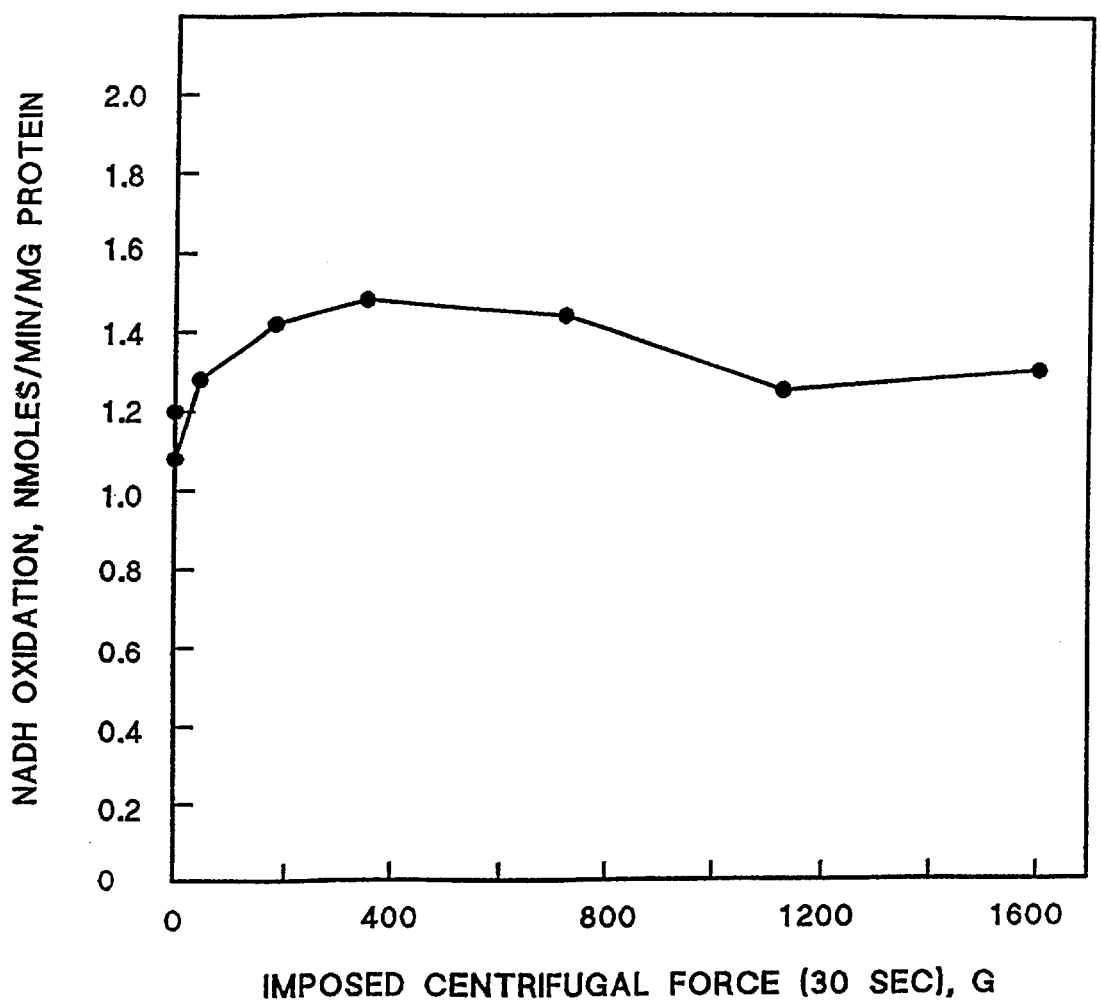
FIG. 3 is a graph showing the NADH oxidation rate in right-side out plasma membrane vesicles isolated from hypocotyl segments as a function of centrifugal force.
Figure 4:
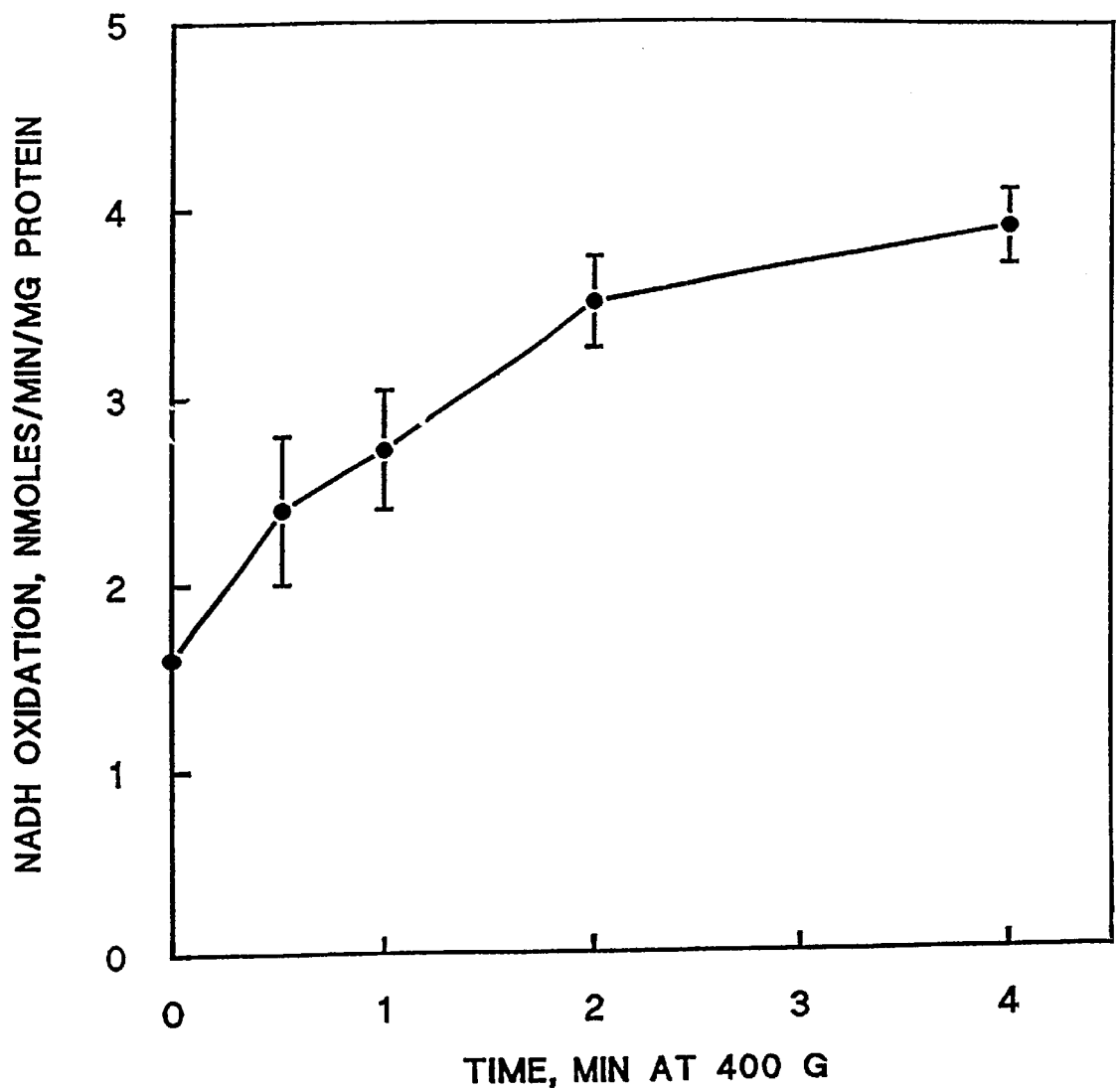
FIG. 4 is a graph showing the NADH oxidation rate in right-side out plasma membrane vesicles isolated from hypocotyl segments as a function of centrifugal time.

Isolated vesicles of plasma membranes also exhibited a response to centrifugation that was both g force (FIG. 3) and time (FIG. 4) dependent. A 50% increase in activity was seen with vesicles centrifuged at about 400 g for approximately 2 minutes. The response to centrifugation persisted for about 8 minutes and then returned to initial rates.

The gravity sensing apparatus of the present invention comprises an NADH oxidase of the plasma membrane, means for measuring the NADH oxidase activity, and means for translating the activity to represent the relative gravitational force exerted on the protein.

The following examples further clarify the invention but are not intended to be limiting.

EXAMPLE 1

Preparation of Soybeans for Use in Isolating Plasma Membranes

Soybean seeds were soaked for 4 to 6 hours in deionized water and planted in moist vermiculite in foil-covered boxes. The seeds were allowed to grow for 4 to 5 days in darkness without supplemental additions of water. Segments approximately 1 to 2 cm were cut 5 mm below the cotyledons under low light. The 1 cm segments were saved for use as whole sections, while the 2 cm segments were used to isolate the plasma membranes.

EXAMPLE 2

Isolation of Plasma Membranes from Soybean Hypocotyls

The 2 cm segments were homogenized using a chilled mortar and pestle in two volumes of medium containing 25 mM Tris-HCL, 300 mM sucrose, 10 mM KCl, and 1 mM $MgCl_2$, at a pH of 7.5. The homogenates were filtered through a single layer of Miracloth to remove debris and cell walls and centrifuged at 5,800×g for 10 min. and the pellet was discarded. The supernatant was then centrifuged at 40,000×g for 30 min. to yield a crude microsomal pellet. Predominantly right-side out plasma membrane vesicles were isolated from the crude microsomal pellet by aqueous two-phase partition using a 16 g system of 16.4% (w/w) polymers (Dextran T500 and Polyethylene Glycol 3350), contained in 0.25 M sucrose and 5 mM potassium phosphate, pH 6.8). Membranes were suspended in 50 mM Tris-Mes, pH 7.0.

EXAMPLE 3

Determination of NADH Oxidase Activity in Soybean Hypocotyls

NADH oxidase activity was determined for 20 1 cm sections of etiolated hypocotyls of soybean seedlings. The incubation mixture consisted of 30 mM Tris-Mes (pH 7.0), 0.6 mM KCN and 90 μM NADH in a total volume of 4 ml. The reaction was started by the addition of NADH. At intervals of 3 min. the solution was mixed by several excursions through a pasteur pipette and a 2.5 ml portion of the incubating solution was removed to a cuvette. The absorbance at 340 nm was determined using a Perkin-Elmer Model Labda 3B spectrophotometer. A millimolar extinction coefficient of 6.22 $mM^{-1}cm^{-1}$ was used to calculate rates of NADH oxidation expressed as nmoles/min/20 sections.

EXAMPLE 4

Determination of NADH Oxidase Activity in Isolated Plasma Membranes of Soybean Hypocotyls The NADH oxidase activity was determined for 0.1 mg plasma membrane protein in 50 mM Tris-Mes buffer (pH 7.0), 150 μM NADH, and 1 mM KCN (to inhibit any mitochondrial NADH oxidases from contaminating the plasma membranes). Due to the low specific activity inherent to the plasma membrane NADH oxidase and the high absorbance of the turbid plasma membrane preparations, absorbance changes at 340 nm were estimated using a full scale of 0.06 O.D. monitored using a Hitachi Model U3210 spectrophotometer. The activity was calculated using an extinction coefficient of 6.21 $mM^{-1}cm^{-1}$.

EXAMPLE 5

Stimulation of NADH Oxidase of Soybean Hypocotyls by Inversion

Twenty etiolated hypocotyl soybean 1 cm sections were cut and placed in 4 ml of solution containing 5 mM Tris-Mes (7.0 pH), 1 mM KCN, and 150 μM NADH. At intervals of 2 min. the incubating solution was mixed and a 2.5 ml portion was transferred to a cuvette and the absorbance at 340 nm was determined. The solution was then returned to the incubation vessel. The sections were oriented right side-up (RSU) for 30 minutes of incubation and inverted and incubated upside down (USD) for 30 minutes. This process was repeated, resulting in two periods of RSU orientation and two periods of USD orientation. Fresh NADH was added after each inversion. (Table 1, FIG. 1).

Although the invention has been described above in relation to preferred embodiments thereof, it will be understood by those skilled in the art that variations and modifications can be effected in these preferred embodiments without departing from the scope and spirit of the invention.

What is claimed is:

1. A method for sensing gravity comprising:

delivering a predetermined quantity of external NADH to a soybean hypocotyl NADH oxidase; measuring the rate of oxidation of said external NADH by said soybean hypocotyl NADH oxidase; and translating said rate of oxidation to represent the relative gravitational force exerted on said soybean hypocotyl NADH oxidase, wherein said gravitational force is below 250 g.

2. The method for sensing gravity according to claim 1 wherein said soybean hypocotyl NADH oxidase is present as part of a plasma membrane.

3. The method for sensing gravity according to claim 1 wherein said soybean hypocotyl NADH oxidase is produced recombinantly.

4. An apparatus for sensing gravity comprising:

a soybean hypocotyl NADH oxidase; means for measuring the rate of oxidation by the soybean hypocotyl NADH oxidase; and means for translating the rate of oxidation to represent the relative gravitational force exerted on the soybean hypocotyl NADH oxidase, wherein said gravitational force is below 250 g.

5. An apparatus according to claim 4 wherein said soybean hypocotyl NADH oxidase is produced recombinantly.

* * * * *